(12) United States Patent
Ehrenreich et al.

(10) Patent No.: US 9,370,306 B1
(45) Date of Patent: Jun. 21, 2016

(54) METHODS AND DEVICES FOR IN VIVO TARGETED LIGHT THERAPY

(75) Inventors: Kevin J. Ehrenreich, San Francisco, CA (US); Kyle Klein, Sunnyvale, CA (US); John Stankus, Campbell, CA (US)

(73) Assignee: ABBOTT CARDIOVASCULAR SYSTEM INC., Santa Clara, CA (US)

(*) Notice: Subject to any disclaimer, the term of this patent is extended or adjusted under 35 U.S.C. 154(b) by 1909 days.

(21) Appl. No.: 12/191,200

(22) Filed: Aug. 13, 2008

(51) Int. Cl.
  *A61N 5/06* (2006.01)
  *A61B 5/00* (2006.01)
  *A61B 5/1459* (2006.01)
  *A61B 18/14* (2006.01)

(52) U.S. Cl.
  CPC .............. *A61B 5/0084* (2013.01); *A61B 5/1459* (2013.01); *A61B 18/1492* (2013.01); *A61N 5/062* (2013.01); *A61N 5/0603* (2013.01); *A61B 2562/0233* (2013.01)

(58) Field of Classification Search
  CPC .... A61B 5/029; A61B 5/0295; A61B 5/0084; A61B 18/1492; A61B 5/0022; A61B 5/021; A61B 5/14546; A61B 5/0075; A61B 5/0275; A61B 5/14532; A61B 5/1459; A61B 19/5244; A61B 2018/00577; A61B 2562/023; A61B 1/00057; A61B 5/02156; A61B 5/1495; A61B 6/58; A61B 6/582; A61B 6/583; A61B 6/585; A61B 2017/00725; A61B 2580/0223; A61B 2580/0228; A61B 26/085
  USPC .......................................... 607/88–89, 90–92
  See application file for complete search history.

(56) References Cited

U.S. PATENT DOCUMENTS

| | | | |
|---|---|---|---|
| 4,009,382 A | 2/1977 | Nath | |
| 5,042,494 A * | 8/1991 | Alfano | 600/477 |
| 5,412,750 A | 5/1995 | Nath | |
| 5,608,834 A | 3/1997 | Van Leeuwen | |
| 5,709,653 A | 1/1998 | Leone | |
| 5,800,478 A | 9/1998 | Chen et al. | |
| 6,749,623 B1 * | 6/2004 | Hsi et al. | 607/88 |
| 6,811,562 B1 | 11/2004 | Pless | |
| 7,131,963 B1 | 11/2006 | Hyde | |
| 7,252,677 B2 | 8/2007 | Burwell et al. | |
| 7,344,528 B1 | 3/2008 | Tu et al. | |
| 2004/0230156 A1 | 11/2004 | Schreck et al. | |
| 2005/0031281 A1 | 2/2005 | Nath | |
| 2005/0070844 A1 | 3/2005 | Chow et al. | |
| 2005/0228260 A1 * | 10/2005 | Burwell et al. | 600/408 |
| 2007/0090272 A1 | 4/2007 | Wang | |
| 2008/0025943 A1 | 1/2008 | Michal et al. | |
| 2008/0027517 A1 * | 1/2008 | Burwell et al. | 607/88 |
| 2008/0033339 A1 | 2/2008 | Tulip et al. | |

OTHER PUBLICATIONS

StockerYale Inc., Laser Line Generators, LEDs, Specialty fibers, downloaded www.stockeryale.com, May 29, 2008, 1 page.
StockerYale Inc., "Custom-Engineered LED Solutions", downloaded www.stockeryale.com, May 29, 2008, 2 pages.

* cited by examiner

*Primary Examiner* — David Shay
(74) *Attorney, Agent, or Firm* — Squire Patton Boggs (US) LLP

(57) ABSTRACT

Catheter-based systems for in-vivo targeted light therapy include a first type of catheter configured for photo-activating photosensitive substances in tissue, and a second type of catheter configured for photo-degrading photosensitive substances in tissue. The catheters may be configured to produce light using a variety of light sources, such as light emitting diodes (LEDs) and fiber optics. The light transmission is directed to tissue in such a way that only portions of tissue in a treatment area are exposed to light, depending upon whether the tissue is diseased or healthy.

9 Claims, 7 Drawing Sheets

METHODS AND DEVICES FOR IN VIVO TARGETED LIGHT THERAPY

BACKGROUND OF THE INVENTION

1. Field of the Invention

This invention relates to methods and devices for using light energy and photo-sensitive substances during the course of a drug therapy.

2. Description of the State of the Art

Photodynamic therapy (PDT) involves the delivery of chemical compound drugs called photosensitizers into tissue and then exciting the photosensitizer in order to enable an energy transfer from the photosensitizer to a nearby oxygen molecule. This produces an excited singlet state oxygen molecule that reacts with nearby bio-molecules. With respect to typical cardiovascular applications of PDT, this reaction causes localized damage in the target atherosclerotic tissue, thereby providing a beneficial effect to the patient.

Photochemical degradation occurs when a compound is exposed to high amounts of light which correspond to the absorbance band of the compound. The general mechanism for this degradation involves the absorption of light energy by electrons in chemical bonds. This energy causes the electrons to move to a higher energy state, which can produce a reactive region in the molecule. These reactive regions are more likely to interact with other compounds, notably oxygen, which can break or alter the chemical bond in the compound, resulting in an overall degradation of the chemical.

SUMMARY OF THE INVENTION

The invention is directed to methods and devices for drug delivery using light to activate one or more drugs and/or to degrade a drug's potency. In either case, the invention teaches various devices and methods for performing targeted drug therapy for various types of anatomy. Among the benefits, devices are provided that can reduce the complexity of a procedure associated with light-based drug therapy, such as PDT, photo-chemical degradation, and activation of a photo-cross-linkable therapeutic loaded hydrogel. Features of the invention provide a safer working environment for light-based drug therapy, improve the ability to deliver light energy sufficient to activate or degrade a drug in tissue, improve the ability to activate or degrade a drug's potency at an intended location, but not elsewhere, reduce a patient's "dark time", which is intended to mean the period when a patient administered with a photo-activated substance must not be exposed to light, and/or enable more precise targeting of tissue for drug therapy.

In accordance with one or more of the foregoing objectives, a device configured to perform light-based therapy, e.g., PDT, may integrate flexible electronics at a distal portion thereof, including light emitters and light detectors. In some embodiments, one or more arrays of light emitting diodes (LEDs) are positioned near a working end of a medical device, e.g. a balloon catheter. The LEDs generate light that excites a photosensitizer and initiates PDT of adjacent tissue. Photodiodes may be used in combination with the LEDs to detect reflected light from the anatomy. Depending on the magnitude of the detected light, the photodiodes may transmit a signal that causes the LEDs to either be powered on or off. In this way, a closed loop control system may be used to perform light therapy, e.g., PDT, in a safe and efficient manner. The closed-loop system may be entirely located at the distal portion of the device.

In accordance with one or more of the foregoing objectives, embodiments of the invention include a catheter configured such that a power supply provides electrical power to a distal portion of a catheter, which is safer and easier to implement than Class III lasers that are sometimes used for light therapy, e.g., PDT. In addition, electrical power leads may be more flexible, and thus more deliverable, than fiber optics that are sometimes used for light therapy, e.g., PDT. Additionally, a closed loop control design according to embodiments of the invention may reduce damage of healthy tissue by deactivating LEDs adjacent to healthy tissue. Additionally, a closed loop control design improves power consumption and optimizes light delivery of a diode array to improve efficiency and efficacy of PDT.

According to one aspect of the invention, there are methods and devices for activating photosensitizers in order to initiate a light therapy, e.g., PDT, photochemical degradation, activation of a photo-cross-linkable therapeutic loaded hydrogel. It is particularly useful in bodily vessels since the disclosed methods and devices enable tracking through small diameter vessels such as cardiovascular vessels.

The invention includes the recognition that with the emergence of drug eluting stents (DES) for the treatment of cardiovascular disease, there exists a potential for drug interactions that may not have been considered in a stent's original design or drug elution profile. For example, if a DES of one drug was used in close proximity to a DES of a different drug, there would exist a potential for a drug interaction which may not have been characterized by either producer of the stents. In another example, if two drug eluting stents were placed overlapping in vasculature, the overlapping region would effectively contain twice the designed dose of drug. This dose may cause a sub-optimal clinical outcome. In another example, the diffusion of a drug away from the drug-eluting source could be reduced to a very local region by exposing the proximal and distal ends of the drug-elution device to a degrading light source.

In accordance with one or more of the foregoing objectives, methods and devices are provided that enable an operator to selectively degrade unwanted drug in blood vessels or other anatomy using light. This is useful in such cases as when a DES or drug coated balloon with a specific active agent, e.g., Everolimus, is placed near a DES with a different active agent, e.g., Paclitaxel. In such cases, an operator may degrade the drug proximal to a prior implanted stent to prevent possible drug interaction. Drug interaction may occur due to drug diffusion into adjacent tissue, one DES overlaps another implanted DES etc. In other embodiments selective degrading of drugs can allow an operator to degrade an excess of the same DES drug, e.g., if two DES stents overlapped, the operator can reduce the possibility of introducing a doubling of the dosage by degrading the drug present in an overlapping region of two DES using light therapy. Other embodiments would allow an operator to focus drug exposure to a very specific region of interest by preventing a diffusion of the drug away from the site of delivery.

In accordance with one or more of the foregoing objectives, a catheter-based system contains two components. One component is a drug delivery device. This device can be in the form of a DES, drug coated balloon, bio-absorbable drug eluting stent, a double balloon with drug perfusion, or any other drug delivering device used in vasculature. The second component would be a light source capable of delivering a specific wavelength or wavelengths of light radiation in a targeted manner. The light source may include light emitting diodes, a fiber optic cable with diffuser, a fiber optic cable with a microlens, thin-film diodes, organic light emitting diodes, or any other light source capable of specific, targeted light dosing. The wavelength(s) of light chosen for treatment may depend on the absorbance band of the drug intended to be degraded. Multiple light wavelengths could be utilized to optimize drug degradation and also the penetration depth of exposure. For instance, longer wavelengths of light, although having less energy, are able to penetrate further into body tissue than shorter wavelengths. Light wavelength and intensity may be optimized in this sense, e.g., longer wavelengths for deeper penetration, shorter wavelengths for high energy, to improve the effectiveness of a treatment. For example, optimized wavelength and intensity can promote efficacy towards reduction of restenosis and improve re-endothelialization and long term DES safety. Both stent and balloon coatings can be chosen for optimal degradation.

A drug coated region could be any drug eluting source, e.g., a stent or balloon coated surface. Tissue would be exposed to light energy by way of windows formed as part of a balloon membrane. Select wavelengths may be allowed to pass through the membrane's windows, while other wavelengths are blocked. In other embodiments, the windows may be transparent, thereby allowing all light to pass through the membrane (in this case the light source may only emit certain bands of light). The grating of the window and/or wavelength of light may be chosen based on the absorbance band for the substance being used. The window(s) or light-blocking location(s) on the membrane would determine the effective area the drug would be allowed to expose at full strength. In one respect, a balloon membrane may be constructed with combinations of light filters, e.g., UV, near infra red (NIR), white light, all light, etc. Diffused light may be used in these embodiments. A distal or proximal light source may be used. It will be appreciated that a broad spectrum of light wavelengths may be delivered toward the tissue in accordance with this invention; however, this may not be ideal since it is generally desirable to limit the energy that is delivered into the tissue to prevent excessive heating, for example.

According to one embodiment, a balloon catheter having a window would be used as a DES delivery device. The window can allow for a certain portion of the drug on the stent length to be deactivated in order to prevent the vessel from being exposed to a double dose of drug.

According to another embodiment, windows may be replaced with light sources attached distally, proximally, or both relative to the balloon. One advantage of this design would be a greater exposure as compared to a light source confined to a pressurized balloon chamber. In these embodiments, a degrading light source can expose larger portions of adjacent to tissue to degrade drug that may have diffused quickly after being deposited at a target tissue.

"Target tissue" refers to the tissue that is diseased or abnormal that will be, or is intended to be, treated by a medical device according to the disclosure. In some embodiments, the medical device is configured to expose the target tissue to light energy, e.g., for photo-activation of a substance present in the target tissue. In other embodiments, a medical device is configured for light exposing healthy tissue that may be present adjacent to a treatment area. A "treatment area" refers to the general location of the target tissue. A treatment area includes, in addition to the target tissue, healthy or normal tissue that is adjacent the target tissue.

In other embodiments, a targeted drug therapy as taught by the invention may be used in vasculature, as well as in cancer treatment for a variety of anatomy. For example, tumors may be treated with a potent compound and the regions proximal to the tumor could be exposed to light of a specific wavelength to decrease the spread of the potent compound to other tissues. For tissues that diffuse drugs rapidly, light could be used to slow or control the diffusion of the drug, limiting its effects to the targeted region.

Most light-activation therapies require a patient to spend many hours without exposure to light due to the reactivity of the photosensitizer used in these therapies. The disclosed methods and devices provide ways in which to expose a patient to a wavelength of light that would degrade, as opposed to activate, a photosensitizer. This feature provides an approach for reducing the amount of photosensitizer in unwanted areas, e.g., skin, and may even reduce the overall half-life of a drug in the body. This can also reduce the "dark time" for the patient, i.e., the amount of time the patient cannot be exposed to light due to the presence of light-activated substances in his/her body.

According to another embodiment, a device may provide both a drug activating wavelength and a degrading wavelength. The drug activating wavelength could be focused on a region requiring therapy, while the degrading wavelength could be used to prevent the spread of a drug to adjacent tissue. This technique may be especially useful during the treatment of a cancerous tumor, as discussed above. For example, a balloon membrane may be configured with multiple light filters (drug-activating and drug-degrading light filters). In another example, a drug-activating light source may be emitted from the balloon and drug-degradation light source emitted from a catheter shaft at distal and/or proximal locations relative to the balloon.

Methods and devices disclosed herein may also be utilized in combination with a delivery of a photo-cross-linkable therapeutic loaded hydrogel (e.g. gel paving or needle injection) via double balloon infusion or coated balloon that is later exposed and polymer gelled.

According to another aspect of the invention, the methods and devices disclosed herein may be utilized for a combined delivery of multiple therapeutics such as an anti-inflammatory drug (e.g. dexamethasone) or -olimus drug in combination with a photosensitizer. For example, "end effects" are known to be especially troublesome in terms of restenosis. It may not be desirable to activate a photosensitizer along an entire length of a stent, since the damage to the vessel may be unwarranted given the therapeutic effect that the stent will provide. However, light-activation at the end regions of the stent may contribute to an overall improvement in therapy, and specifically, to a decrease in restenosis at the stent ends. A stent may therefore be photo-activated by directing light of a select wavelength towards a portion of the tissue in a treatment area, so as to activate a previously delivered photosensitizer at the ends.

According to one embodiment, a catheter having distal and proximal portions includes a balloon, or a balloon and stent, located at the distal portion, and a light emitting member located adjacent the balloon. The balloon and light emitting member are configured such that a first portion of the tissue is prevented from receiving light while a second portion of the tissue is exposed to light. The light emitting member may include a plurality of light-emitters and light detectors, and a control system disposed at the distal portion and configured for activating the light-emitters based on signals received from the light-detectors. The light-emitters are light-emitting-diodes (LEDs) and the light-detectors are photodiodes. In other embodiments the balloon has a membrane formed from balloon material, such that the balloon material forms a first balloon portion configured to block all light transmission or allow transmission of light at a first wavelength, and the balloon material forms a second balloon portion configured to allow transmission of light at a second wavelength. The first and second wavelengths may correspond to near infra red, IR, visible and/or UV light wavelengths.

According to another embodiment a catheter having distal and proximal portions and configured for treating tissue in a treatment area, means for producing light at the distal portion, and means for exposing only a portion of the tissue in the treatment area to the light. The means for exposing only a portion of the tissue in the treatment area to the light may include logic located at the distal portion of the catheter and configured for selective illumination of tissue. The means for producing light may include light emitters and light detectors, and the means for exposing only a portion of the tissue in the treatment area to the light may include turning a portion of the light detectors on or off depending on one or more signals received from the light detectors. The means for exposing only a portion of the tissue in the treatment area to the light may include a balloon having a light blocking portion and a light admitting portion. The means for exposing only a portion of the tissue in the treatment area to the light may also include a balloon and light guides disposed distally and/or proximally of the balloon.

According to another embodiment, a method of in vivo light therapy using a catheter includes the steps of locating a balloon of the catheter at a treatment area, wherein at least a portion of the balloon is located opposite a target tissue, and exposing only a portion of tissue in the treatment area to light energy using a light member, wherein the remaining tissue in the treatment area is not exposed to light energy either because the tissue is not opposite activated portions of the light member or the remaining tissue is shielded from the light energy. This method may further include the step of producing a signal in response to light emitted from the light member, and initiating light therapy including emitting light from the light member if the signal is equal to a first value and not emitting light if the signal is equal to a second value. The locating step may include placing a surface of the balloon having a drug disposed thereon in contact with a target tissue, and then exposing only the tissue adjacent the target tissue to light energy. The method of in-vivo light therapy may also include illuminating tissue adjacent the target tissue including transmitting light from a first balloon portion, or transmitting light from a light emitting member located distally and/or proximally of the balloon.

The method of in vivo light therapy may include deploying a first drug eluting stent (DES) mounted to the balloon, and then exposing to light energy only the tissue that is opposite an end of the implanted first DES. The DES may be deployed adjacent a second, previously implanted DES. The second DES may place a first drug in tissue and the first DES may place a second drug in the tissue. In this embodiment, the exposing to light energy step degrades one of the first and second drugs.

According to another embodiment, a catheter's balloon has a membrane wall including a first wall portion formed from a material that transmits light of a first wavelength and a second wall portion that transmits light of a second wavelength or substantially prevents all light transmission; and the catheter includes a light emitting membrane disposed within the membrane. The catheter may further include a stent mounted on the balloon.

According to another embodiment, a method for treating tissue using a drug eluting stent (DES) includes the steps of deploying the DES in a vasculature containing a target tissue and exposing tissue located opposite an end of the deployed stent to light energy. The exposing tissue step may include exposing tissue to drug-degrading light energy. The deploying step may include deploying the DES adjacent a second DES.

One or more of the foregoing features of invention may also be practiced in the context of other in vivo procedures that rely on a targeted, local delivery of a drug in a blood vessel or other anatomy.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 3A depicts the light emitted from the LEDs and reflected towards the photodiodes when the balloon catheter's distal portion is positioned at a treatment area that has both abnormal and healthy tissue. FIG. 3B depicts a distribution of lighting corresponding to the locations of abnormal tissue and healthy tissue.

DETAILED DESCRIPTION OF THE INVENTION

According to one aspect of the disclosure a catheter includes on-board electronics including an array of light-emitters and light-detectors. The electronics may be located at a distal portion such that a substantial amount of control of the light-emitters and light-detectors resides at the distal portion of the catheter. In some embodiments, the electronics are configured to provide closed-loop control of the light-emitters. In this way, the catheter may determine the desired light distribution on tissue that contains photo-degraded and/or photo-activated substances. In a preferred embodiment, the catheter's on-board electronics decide whether to turn on, or turn-off a light-emitting diode (LED) based on the differences between the magnitude of reflected light between healthy and abnormal tissue.

Figure 1:
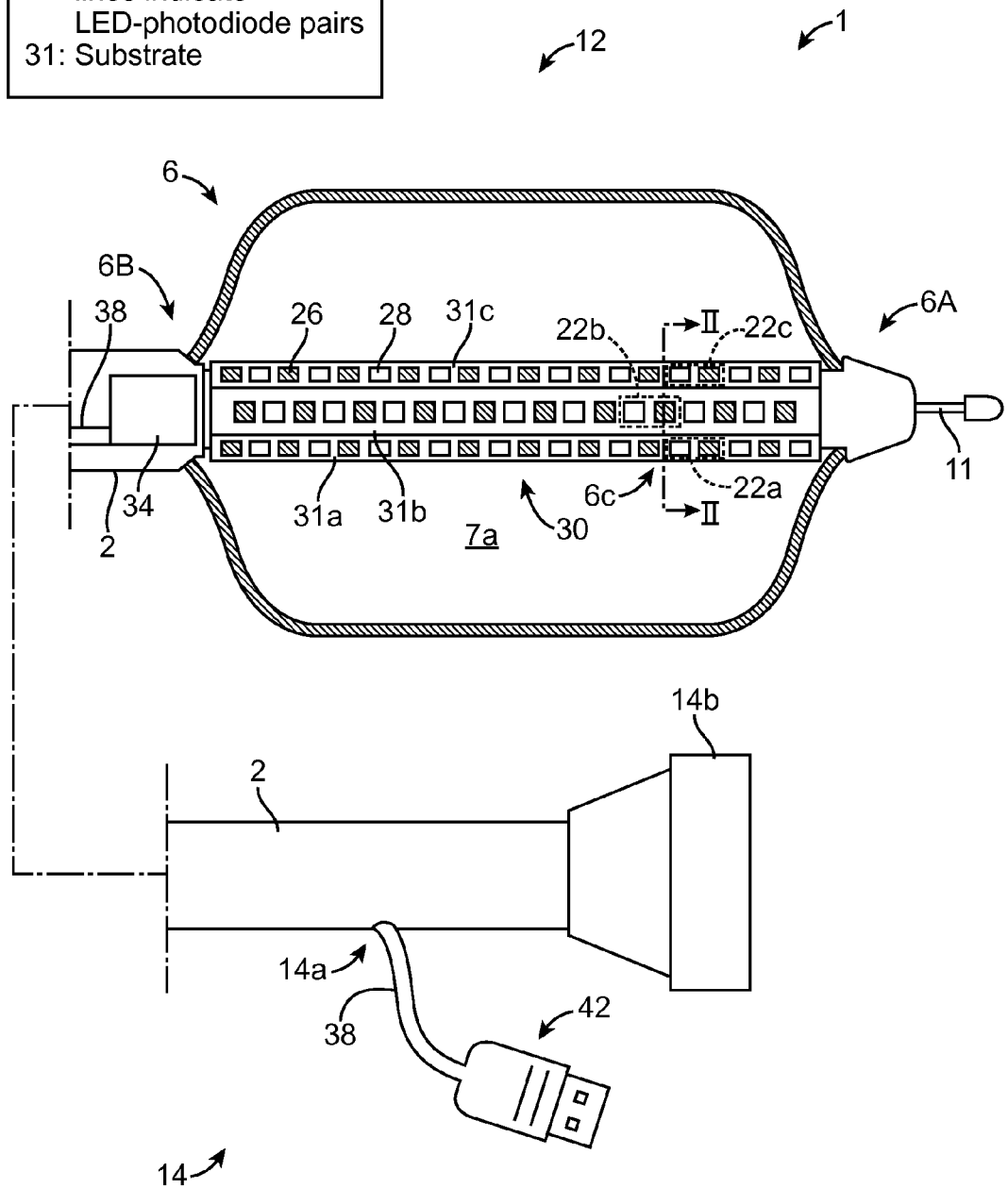
FIG. 1 is side, partial cross-sectional view of one embodiment of a balloon catheter according to the disclosure.
Figure 2:
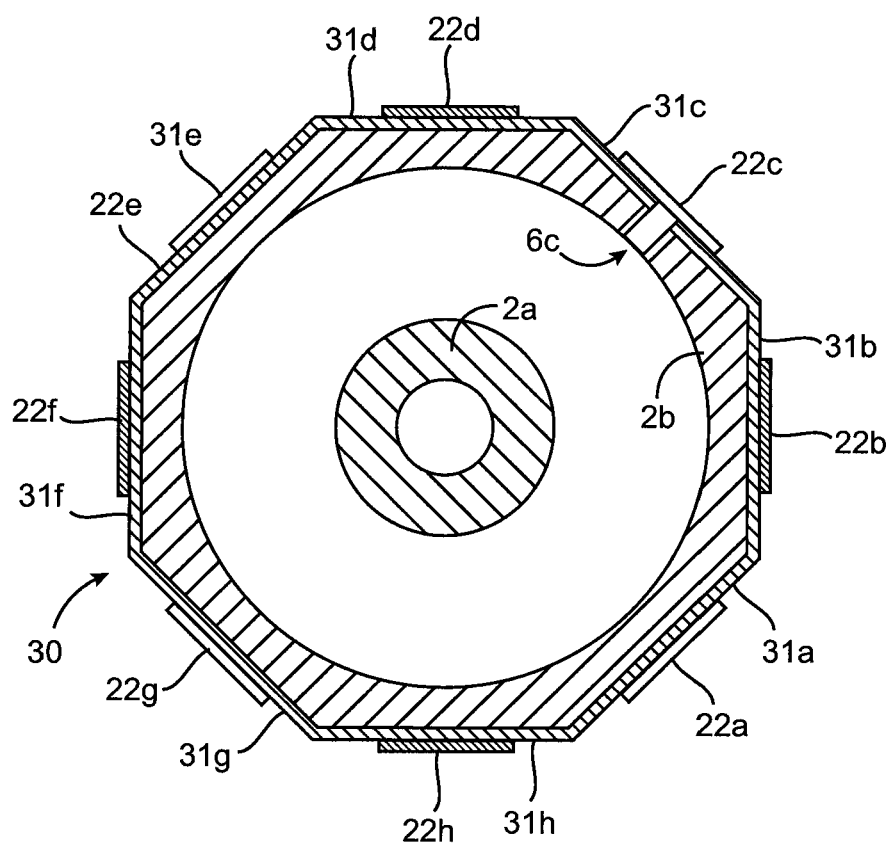
FIG. 2 is a front cross-sectional view of the balloon catheter taken at Section II-II in FIG. 1.

FIG. 1 depicts a side, partial view of a balloon catheter 1 shown in partial cross-section. FIG. 2 depicts a frontal cross-section of the catheter 1 taken at section II-II in FIG. 1. The catheter 1 has a distal portion 12 and a proximal portion 14. A balloon assembly 6 resides at the distal portion 12. A shaft 2, which may be a composite shaft constructed to achieve a desired flexibility, rigidity, deliverability, etc. extends from the distal portion 12 to the proximal portion 14 of the catheter 1.

Various lumens are formed by the shaft 2. These lumens, which are formed over a portion or approximately the length of the catheter shall generally be referred to as aspects of shaft 2, e.g., shaft body portion 2a, 2b, etc (see below). However, the disclosure is intended to encompass any catheter known in the art that is capable of providing the required lumens and performing the specified functions of those lumens in accordance with the disclosure. As such, the disclosure is not limited to a particular type of catheter. Rather, it applies to, e.g., a unitary or composite-type catheter, Over-The-Wire (OTW) or Rapid-Exchange (RX) type catheter, etc. Examples of balloon catheters are described in U.S. Pat. No. 7,131,963 and US Pub. No. 2008/0025943. A guide wire 11 is used to guide the catheter 1 to a treatment area that includes the target tissue. In an alternative embodiment, catheter 1 may be a fixed-wire type catheter that does not require guide wire 11 for guidance through a patient anatomy.

Referring to the cross-sectional views in FIGS. 1 and 2, at the distal portion 12 a tubular body portion 2b of shaft 2 extends from a proximal end 6b of the balloon portion 6 to a distal end 6a thereof. Body 2b defines the portion of the balloon's inflation lumen between ends 6a and 6b. The outer surface of body 2b may have a multi-sided face, e.g., 8-sided, for purposes of mounting electronics as will be discussed shortly. Body 2a defines the portion of the catheter's guide wire lumen between ends 6a and 6b. Bodies 2a, 2b may be portions of a composite or integral shaft.

The balloon 7 may be made of material that can transmit broadband or narrow-band light. Hence, the balloon membrane may be constructed from a transparent-type balloon material so that very little light energy is reflected or absorbed by the membrane; or the balloon material may be constructed from a material that absorbs or reflects light of certain wavelengths, while allowing light of other wavelengths to pass through. Balloon material possessing a combination of light filtering properties may also be desirable. Preferably, a folded or pleated balloon type is used. This is primarily to ensure that light transmissive and opaque segments are accurately placed during inflation, since the balloon of this invention need not be a high pressure balloon. Thus, compliant balloons may also be used, which may not require folding or pleating but instead will be configured significantly circumferentially at all operational diameters. The ends of the balloon 7 are secured at ends 6a, 6b to shaft 2 by, e.g., an adhesive; however, in an alternative embodiment, the balloon ends 6a, 6b may be secured to the shaft using other chemical or thermal welding processes The balloon 7 is inflated by a fluid delivered to the balloon via the inflation lumen (formed in-part by body 2b). Body 2b includes an aperture 6c which puts the inflation lumen in fluid communication with balloon chamber 7a. Thus, as a fluid (gas or liquid) is passed through the inflation lumen the fluid exits through aperture 6c to pressurize the balloon 7. The balloon 7 is shown in a fully expanded state in FIG. 1.

Referring to FIG. 1, the catheter 1 includes arrays of light emitters (e.g., light emitter 28) and light detectors (e.g., light detector 26) disposed on substrates 30. These light emitters and detectors are used to selectively photo-activate agents in tissue. One aspect of the catheter 1 according to the disclosure is the on-board ability at the distal portion 12 to selectively turn on or off light emitters as the catheter 1 is positioned near the treatment area. In this way, the catheter 1 can produce an energy flux only at, e.g., the target tissue, based on a distribution of light received over the body 2b of the catheter 1. This light is detected by the light detectors.

Referring to FIGS. 1 and 2, a plurality of semiconductor substrates 30 are arranged on the exterior surface of the body 2b or integral with the outer surface of body 2b. Each of the substrates 30, e.g., substrate 31a, preferably contain several Light-Emitting-Diodes (LEDs) for emitting light and photodiodes for detecting light. In other embodiments, the light source may include thin-film diodes, organic light emitting diodes, or any other light source capable of specific, targeted light dosing and disposed on a circuit board meeting the footprint requirements of a catheter intended for in vivo light therapy. The wavelength(s) of light chosen for treatment may depend on the absorbance band of the drug intended to be activated or degraded.

The LEDs and photodiodes are arranged in longitudinally extending strips so as to provide an LED array light emitting and photodiode light-detecting capability over the catheter length extending between ends 6A and 6B. These LEDs and photodiodes may be operated by a controller unit 34 disposed at the distal portion 12. The catheter 1 may include a power cord 38 that provides power to a controller 34 and circuitry associated with LED and photodiode chips. The controller 34 may be formed by depositing material onto a plastic substrate in order to form a flex circuit. Since the substrate is flexible, it may be formed radially about the catheter body. One example of material that is suitable for a flex circuit substrate is Polyimide. The power cord 38 may pass through the inflation lumen. At the distal portion 14 the power cord 38 exits through a port 14a. A connector 42 may be provided to connect the power cord to a power source. As depicted, the catheter may include eight longitudinally extending substrates, i.e., 31a-31h, that are disposed on eight sides of body 2b (FIG. 2). Each substrate has an array of photodiode-LED pairs. For instance, in the cross-sectional view of FIG. 2 LED-photodiode pairs 22a-22h correspond to one of the LED-photodiodes disposed on each of the respective substrates 31a-31h. The substrates 31 may be integrated into the body 2b or adhered, attached, etc. to the body 2b. The substrates 31 and/or body 2b may include heat sinks that transfer heat generated by the LEDs to an inner lumen, e.g., inflation lumen, by way of metallic heat paths extending radially through body 2b. Transfer or heat isolation may also be achieved by a circulating fluid, e.g., inflation fluid, or flushing fluid passed through, e.g. the lumen formed by body 2b.

A substrate such as substrate 31a may correspond to a portion of a circuit board including other substrates, e.g., adjacent substrates 31b and 31h, or an individual circuit board having its own input/output for electrically communicating with the controller 34. In a preferred embodiment, a circuit board may contain several tightly packed LED/photodiodes manufactured by Stocker Yale, Inc., 32 Hampshire Road, Salem, N.H. 03079 (http://www.stockeryale.com/i/leds/). Each array 31a-31g may correspond to such a circuit board.

As was just recently mentioned, each LED may be paired with a photodiode as in, e.g., LED-photodiode pairs 22a, 22b, and 22c (LEDs are distinguished from photodiodes in the drawings by hash-marks over photodiodes). The pair may be designed to operate as follows. The LED portion emits light towards adjacent tissue. Light reflected, emitted or scattered from the tissue is detected by the adjacent photodiode. The amplitude of this light energy is then communicated to the controller 34 from the photodiode by an electrical signal that is proportional to the magnitude of the detected light energy. The controller 34 may then be programmed to turn the LED "on" or "off" based on the magnitude of electrical signal received from the photodiode. By placing the LED and photodiode in pairs, the controller 34 may need only simple logic since it may in some cases be assumed that light detected at a photodiode originated substantially from the adjacent or closest LED. For example, the controller 34 logic may assume that whenever a signal above a certain threshold is produced by the photodiode portion of LED-photodiode pair 22a, the signal was caused substantially by the LED portion of this pair, i.e., the closest LED. Other logic may be used to determine which LED lights were the cause of a signal produced by a photodiode.

A catheter according to the disclosure need not assume that the majority of light received by a photodiode was the result of light emitted from the adjacent LED. For instance, the catheter 1 may execute an on-board diagnostic or calibration routine before reaching a treatment area to determine how LED light is reflected from tissue when the catheter is placed in similar anatomy, e.g., similar vasculature, as the treatment area (absent the abnormal tissue). The controller 34 would initiate an on-off cycle over all LEDs, recording the magnitude of the signal produced at a photodiode during the brief time that each individual LED is the only LED emitting light. Then, the LED corresponding to the highest magnitude electric signal produced by the photodiode is designated as the LED that will be turned on/off based on the signal received from this photodiode. This procedure may then be repeated for all photodiodes. At the end of this calibration, the controller has assigned or cross-referenced one or more LEDs with a signal produced at each of the photodiodes. Accordingly, when the catheter arrives at the treatment area, the controller determines which LED(s) to turn on or off by cross-referencing the photodiode signals with the corresponding LED(s).

The logic according to the disclosure may therefore be used to determine which LEDs to de-energized or turn off when the electrical signal produced by a photodiode is above a certain threshold. "On/off" signal commands to LEDs may be produced by the controller 34 by opening/closing switches, and the photodiode signals communicated to the controller 34 in order to decide which LEDs should be turned on or off. In some embodiments the controller 34 may have programmable logic or hard-wired (i.e., non-programmable) logic.

In other embodiments a controller may not be needed. According to these embodiments, a substrate may include circuits that have their own logic built-in for deciding whether an LED remains on or off. For example, for an embodiment that has LED-photodiode pairs, a signal produced by the photodiode may turn off the adjacent LED if the signal magnitude reaches a threshold level. Again, this design assumes that the light detected by the photodiode is always due in substantial part to the light emitted by the adjacent LED. Under these embodiments the LED-Photodiode pairs on a substrate may operate as autonomous units.

The catheter may have a 1:1 ratio of LED chips to photodiode chips, e.g., as in the embodiments of arrays of LED-photodiode pairs. In other embodiments the ratio may be 2:1 (meaning two LED to every photodiode), 3:1, 4:1. The selected ratio and logic used to determine which LEDs to turn on/off may depend on the type of anatomy being treated. For example, irregular or unpredictable light scatter or reflection properties due to the geometry of the anatomy may require more sophisticated logic. When the walls of an anatomy are smooth, and cylindrical like (as in the illustrated example), then a more simple logic may be the preferred choice.

Figure 3A:
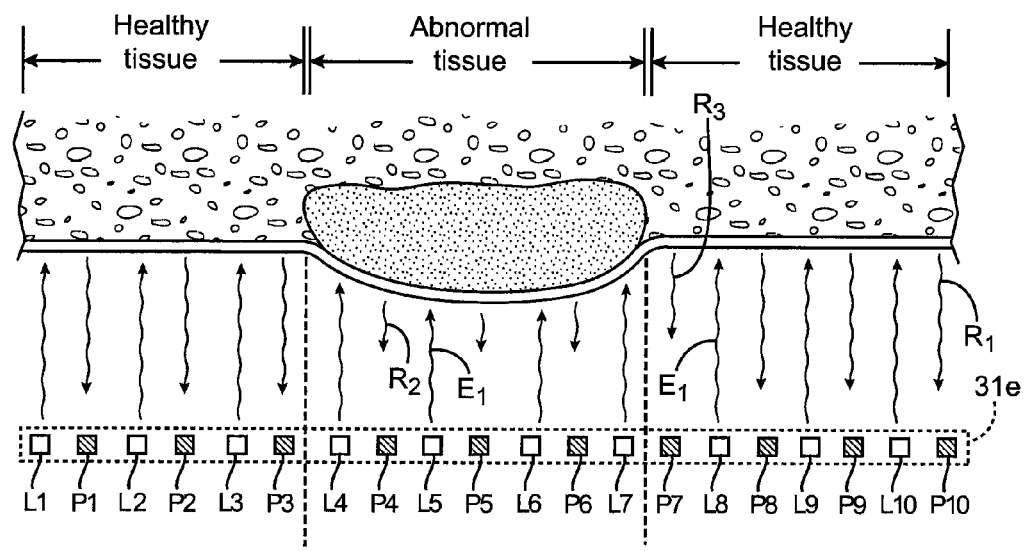
FIGS. 3A-3B are schematic illustrations of features associated with an array of light emitters (e.g., LEDs) and array of light detectors (e.g., photodiodes) located at a distal portion of the balloon catheter of FIG. 1.
Figure 3B:
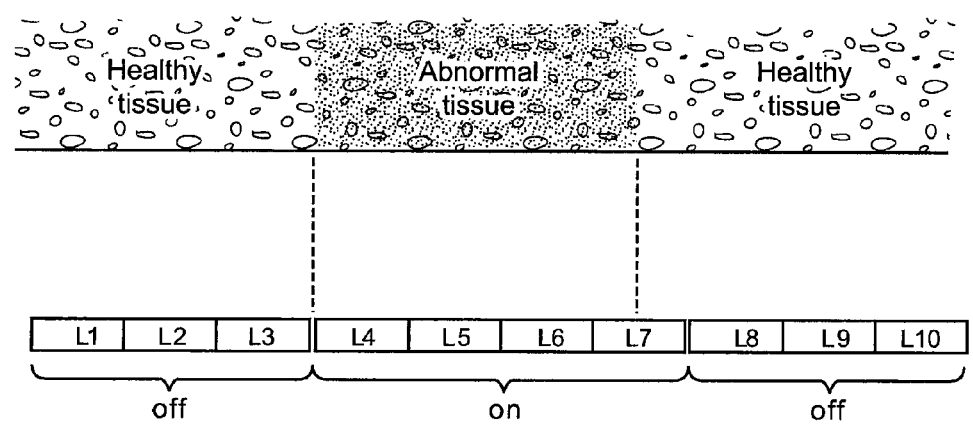

FIGS. 3A-3B illustrate schematically aspects of embodiments just described. FIG. 3A depict the light intensities of the emitted and reflected light for LED-photodiode array 31c from FIG. 1. For ease of illustration, the balloon 7 of the catheter 1 is not drawn in FIG. 3A. Here the LEDs for array 31c are designed by clear boxes and referred to as L1, L2, L3, L4 . . . L10. The photodiodes are designated by hash boxes and referred to as P1, P2, P3, . . . P10. Opposing the array 31c is a section of tissue. The intensity of emitted light from each of the LEDs is E1 and the intensity of the reflected light is R1, R2 or R3.

A section of tissue opposing LEDs L4, L5, L6 and L7 contains abnormal tissue, whereas the section of tissue opposing LEDs L1-L3 and L8-L10 is healthy. Because a tumorous tissue can have different light reflecting properties from healthy tissue, the reflected light for P4-P7 is significantly different in magnitude from P1-P3 and P8-P10. In particular, the healthy tissue will tend to reflect more light than the abnormal tissue. As such, there is a higher return energy flux detected by photodiodes that receive light reflected from healthy tissue. This is depicted in FIG. 3A by the different intensities of reflected light R1, R2 and R3 in FIG. 3A. The light emitted from the LEDs is depicted by E1.

Distinguishing light characteristic of tissue may be used as the criteria to selectively turn on or off LEDs. Thus, a local presence of a tissue type, or transition between tissue types may be inferred based on the signals produced by photodiodes in response to the variation in reflect light intensity. FIG. 3B depicts the distribution of LEDs turned "on" verses those turned "off" as a result of the reflected light distribution depicted in FIG. 3A. Since photodiodes P4-P7 received an amount of reflected light resulting in an electrical signal having a magnitude less than some predetermined amount (call it "X"), the LEDs associated with these photodiodes were turned on to photo-activate a photo-sensitive substance in the tissue, i.e., the abnormal tissue opposing LEDS P4-P7. The LEDs associated with P1-P3 and P8-P10 are turned off since the magnitude of the light energy detected by these photodiodes resulted in an electrical signal above the threshold X (indicating the presence of healthy tissue).

In other embodiments, a detected magnitude of light energy above a threshold may instead cause an LED to turn on, rather than off. For example, when light energy is desirable for purposes of degrading a drug's potency in healthy tissue that is adjacent to cancerous tissue, but without affecting the drug's potency in the cancerous tissue, LEDs would be turned on if the magnitude of the electrical signal at the corresponding photodiode is greater than X.

As depicted in FIG. 3A, the LED-photodiode pair (L7, P7) is located at a transition zone between healthy and abnormal tissue. In this area, the reflected light R3 may produce an electrical signal much greater than the signal corresponding to R1 yet still less be less than the threshold X. In the examples described above, L7 would be turned on since the magnitude of the signal is less than X. In other embodiments a criterion for turning on/off an LED may instead be based on whether the signal falls within a range of values, as opposed to whether it is above or below a single value. In still other embodiments, a mean of several received electrical signals may be compared to a value. These signals may be obtained from changes in the light distribution resulting from slight perturbations in the catheter's placement. Related criteria for turning an LED on/off would be to protect healthy tissue as the priority over ensuring that the substance in the abnormal tissue is everywhere photo-activated, in which case L7 may instead be turned off since it appears to cover healthy as well as abnormal tissue (or, in the case of when healthy tissue is being protected by supplying a drug-degrading light energy, L7 would be turned on). Other criteria for turning LEDs on or off would be the optimization of the available power. When less LEDs are used, the available energy flux per LED goes up for a constant source of available power supplied to the distal portion 12. It may be more effective to deliver a higher energy flux per LED by turning off LEDs that may be positioned opposite both healthy and abnormal tissue (rather than turning on LEDs that illuminate both abnormal and healthy tissue) so as to ensure photo-activation (or photo-degradation, as the case may be) of at least some of the photo-sensitive substance.

Figure 4:
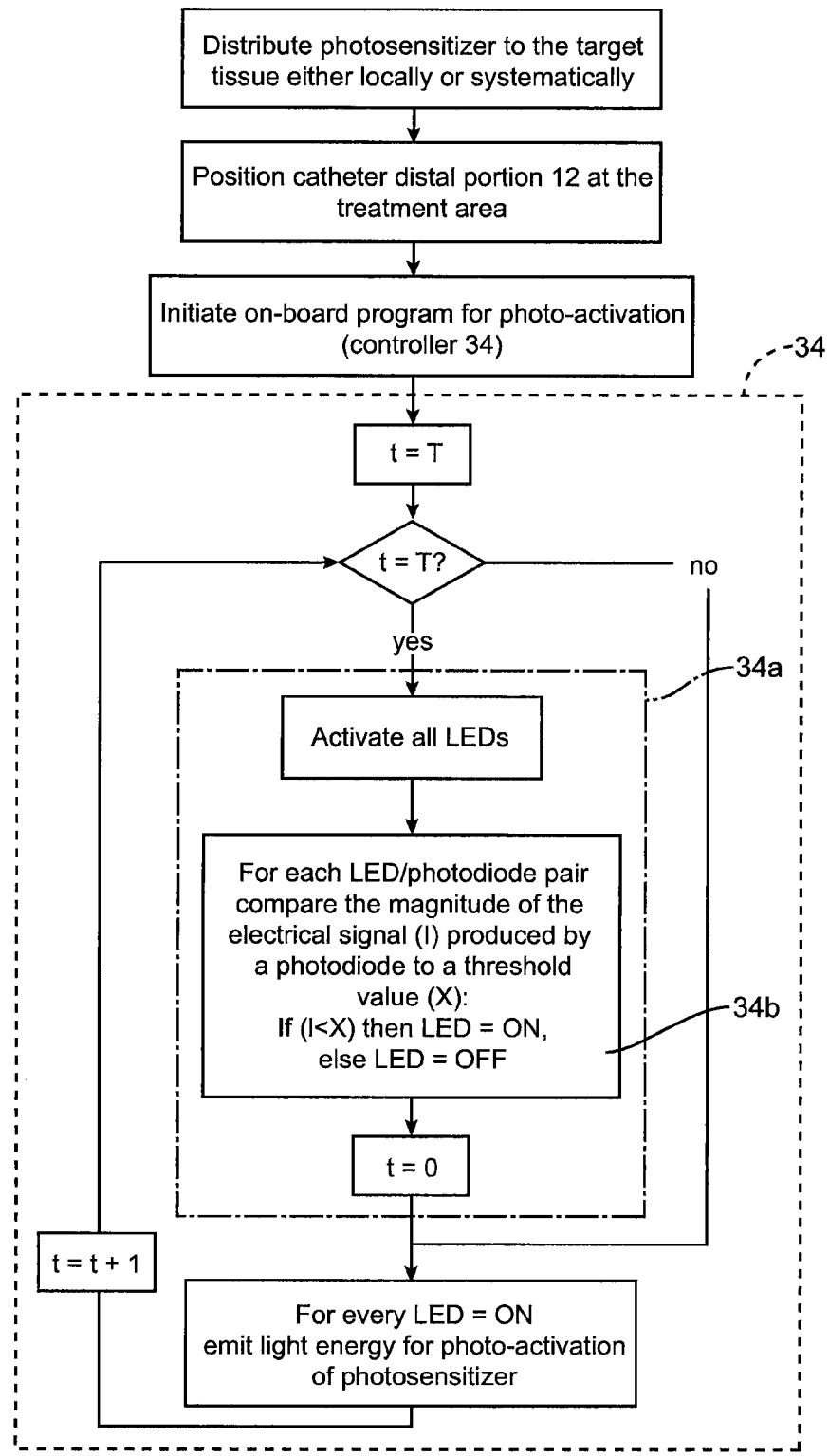
FIG. 4 is a flow diagram relating to a procedure for performing light therapy on a target tissue.

A method for activating photosensitizers absorbed in abnormal tissue, but not adjacent, healthy tissue is depicted in the flow diagram of FIG. 4. A photosensitizer is deposited, injected, etc. into the body such that tissue at the treatment area absorbs this photo-sensitive substance. Next, the catheter 1 is delivered to the treatment area, e.g., percutaneously. The balloon 7 is then inflated and pressed against the tissue. This provides a light path from/to the light detectors and emitters. As such, the balloon 7 may be thought of as a blood-displacement feature for displacing blood from the treatment area so that there is a clear line of sight between a LED/photodiode and opposing tissue. Preferably, neither the inflation fluid nor the balloon membrane diffuse, refract or reflect any appreciable amount of light.

The operator may then initiate the on-board control, e.g., supply power to controller 34. When on-board control begins, a determination is made as to which LEDs are positioned opposite healthy tissue and/or which LEDs are positioned opposite abnormal tissue, e.g., lipid-rich tissue such as atheroma which tends to absorb and scatter more light than healthy tissue. LEDs may thereafter be controlled by a closed-loop electronic control system residing at the catheter distal portion 12. The program may be initiated by communicating a "start" signal from the proximal portion 14 to the controller 34 or simply energizing a circuit located at the distal portion 12. Once initiated, LEDs may be controlled autonomously by the controller 34. According to these embodiments the operator need not monitor or decide which individual LEDs are turned on/off during the therapy. For example, any of the examples of logic and circuit architecture disclosed earlier, including the controller 34, circuit board 30 (or both) may be programmed to decide which LEDS should be turned on to photo-activate the substance in tissue and/or which LED should be turned off based on, e.g., an electrical signal corresponding to a threshold reflected light intensity "X", on-off cycling of LEDs, etc. (as discussed earlier). Further examples follow.

As depicted in FIG. 4, after initiating the controller 34 a timer "t" is initially set to a constant T. The controller 34 then performs a calibration routine 34*a* because "t=T". This calibration routine may first turn "on" all LEDs then decide which LEDs to turn "off". For example, the controller 34 activates all LEDs and then turns off any LED where the signal produced at the corresponding photodiode (e.g., photodiode P1 of the LED-photodiode pair (L1, P1) depicted in FIG. 3A) exceeds a maximum value X (as depicted schematically in block 34*b* of FIG. 4). For embodiments of a medical device intended to supply light energy for purposes of drug degradation (as opposed to drug-activation), block 34*b* would instead turn on an LED if the electrical signal exceeded the value X.

After this initialization routine, the LEDs that were set to "ON" are used to photo-activate substance in the tissue while the remaining LEDs are left off. After a period of time has elapsed equal to, or exceeding T (as depicted schematically by the counter "t=t+1" and decision point "t=T?") the calibration routine 34*a* is repeated. Preferably, the calibration routine is repeated on a regular basis to automatically account for any intentional or unintentional movement of the catheter in the body. Further, it is contemplated that the calibration routine may be sufficiently brief to avoid significant unintentional activation or degradation of photosensitizer should there be intentional or unintentional movement of the catheter in the body. As such, the light distribution may automatically update without requiring direct operator involvement.

The bandwidth of light used to photo-activate may be NIR, IR, visible or UV. The catheter 1 may also include a circuit for communicating a control signal to the operator that indicates the number of LEDs that the controller has decided should be used to treat tissue (transmitted over cable 38). From this information the operator may control/monitor the energy flux per unit area being supplied to tissue. In other embodiments the controller 34 may be programmed to control the power supplied to the LEDs to ensure that the energy flux does not exceed a maximum, or to optimize the LEDs turned on/off as a function of the range of energy flux needed to treat tissue, e.g., between 15-50 J/cm$^2$.

According to others aspect of the disclosure, a catheter includes a light source, or is coupled to an extracorporeal light source. The light emitted from the catheter at its distal portion may be filtered by a filter provided by the balloon membrane according to some embodiments. In other embodiments a catheter has a light emitting member at a location distal and/or proximal of a balloon. A catheter according to these embodiments may be used to achieve a desired activation or degradation of a photo-sensitive substance using light energy. Methods according to these embodiments include the delivery of a drug coated balloon or DES to a target tissue.

Figure 5:
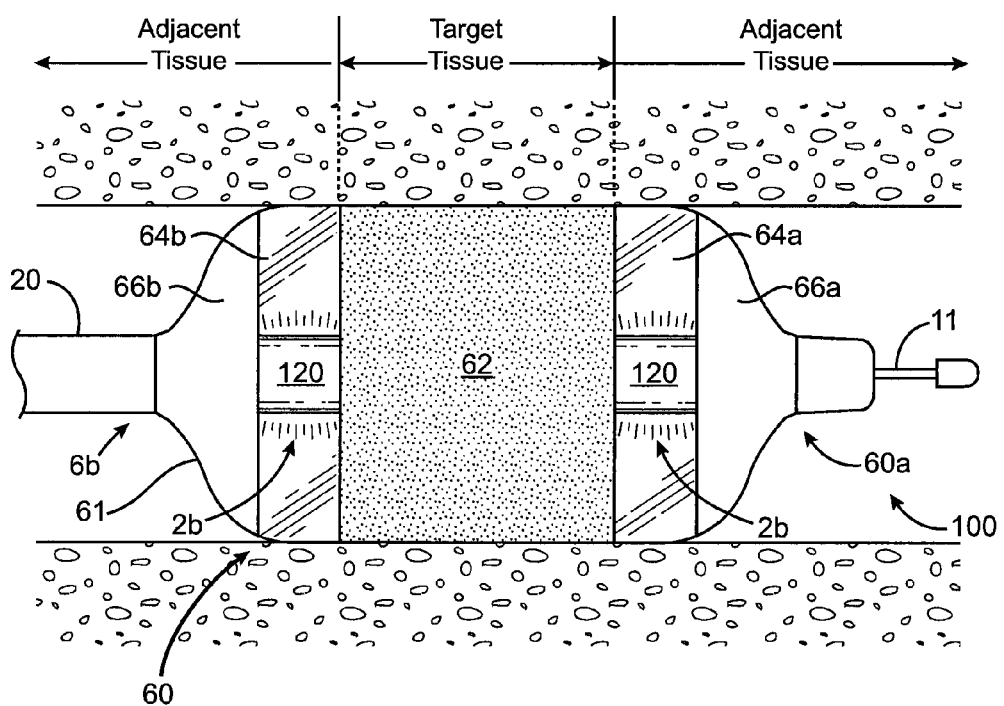
FIG. 5 is a partial view of a balloon catheter located at a treatment area according to another aspect of the disclosure.

Referring to FIG. 5, a balloon catheter 100 is depicted within a vessel with its balloon in the expanded state. The catheter 100 is guided to this treatment area along the guide wire 11 (as before). Unless noted below explicitly or implied by the context of the discussion, as will be appreciated, the catheter 100 possesses the same features as embodiments of catheter 1 discussed earlier.

Catheter 100 includes a light source that is capable of emitting light 120 from body 2*b*, which as before may extend between ends 6*b*, 6*a* and within the balloon chamber 7*a* (see FIG. 1). Light may emit over the entire length of the body 2*b*, or only at select portions, such as nearest ends 6*a*, 6*b*. The light source may correspond to an LED array (as described earlier) or fiber optics. In the later case, a fiber optic bundle may be configured to transmit light originating at the proximal portion 14 of the catheter to a location near end 6*b*, e.g., by passing the fiber optic bundle through the inflation lumen. From this point, the body 2*b* may be configured to transmit light from its outer surface. Light collectors and/or diffusers may be incorporated into body 2*b* to improve/enhance the light distribution as it exits the fiber optics. For example, a focusing lens can first collect light exiting from the fiber optics, followed by a diffusion lens, which forms the outer surface of 2*b*. A diffusion lens can provide uniform illumination of the surrounding tissue. An LED array may instead be chosen over fiber optics so that, e.g., light transmission losses from the proximal portion 14 to the distal portion 12 are reduced. This LED array may be constructed on the same type of circuit as discussed earlier in connection with FIGS. 1-3. Additionally, for embodiments of catheter 100 the array(s) may contain only LEDs, i.e., the circuit board(s) need not also include photodiode chips; although in some embodiments photodiodes may be used as this can provide additional advantages in view of the disclosure. Examples of suitable light sources for light-emitting catheters are described in U.S. Pat. No. 7,344,528, U.S. Pat. No. 5,800,478, U.S. Pat. No. 7,252,677 and U.S. Pat. No. 6,749,623.

According to embodiments of the catheter 100, the membrane 61 of balloon 60 may have a combination of balloon membrane material (i.e., the portions 62 and 66b, 66a) that substantially prevent all wavelengths of light from passing through the membrane walls, and membrane material, or windows 64b, 64a that permit a wide or narrow bandwidth of light to pass. As such, tissue may be exposed to light energy at locations where windows, e.g., 64b and 64a, are present while portion 62 prevents light energy within the balloon from reaching tissue. Portions 66 may be opaque.

According to the following example (depicted in FIG. 5), the catheter 100 is used to supply drug-degrading light energy to healthy tissue. As such, the light-blocking portion of the balloon membrane (portion 62) is placed opposite the target tissue and the windows 64 opposite the healthy tissue. In other embodiments, the catheter 100 may be configured to provide drug-activating light energy to a target tissue. For these embodiments, portion 62 may be made from transparent balloon material and portions 64 from light-blocking balloon material.

In the case of supplying drug-degrading light energy according to some embodiments, a drug, e.g., Everolimus, is combined with a photosensitizer and deposited on portion 62. The objective is to deposit a full dosage of active drug to the target tissue but not the surrounding tissue (designated "adjacent tissue" in FIG. 5). This is achieved by exposing the adjacent tissue to light that degrades the drug's potency (due to the activation of a photosensitizer) should any drug diffuse or otherwise come in contact with the adjacent, healthy tissue. By this approach an undesirable presence of the drug at the adjacent tissue can be dealt with by degrading the drug's effectiveness using light, e.g., UV light.

According to one method the catheter 100 is positioned so that portion 62 is located at the target tissue. The balloon is expanded to place the drug (deposited on the surface 62) in contact with the target tissue. The light source is then activated and light 120 emits from body 2b. The tissue on each side of the target tissue is exposed to light since in this case windows 64 are located near ends 6b, 6a. The target tissue is opposite the light-blocking membrane portion 62. Therefore, the target tissue does not receive the drug degrading light whereas the adjacent tissue does receive this light. After an energy flux has been achieved sufficient to activate photosensitive material in the adjacent tissue, the drug's potency in the adjacent tissue is reduced.

Figure 8:
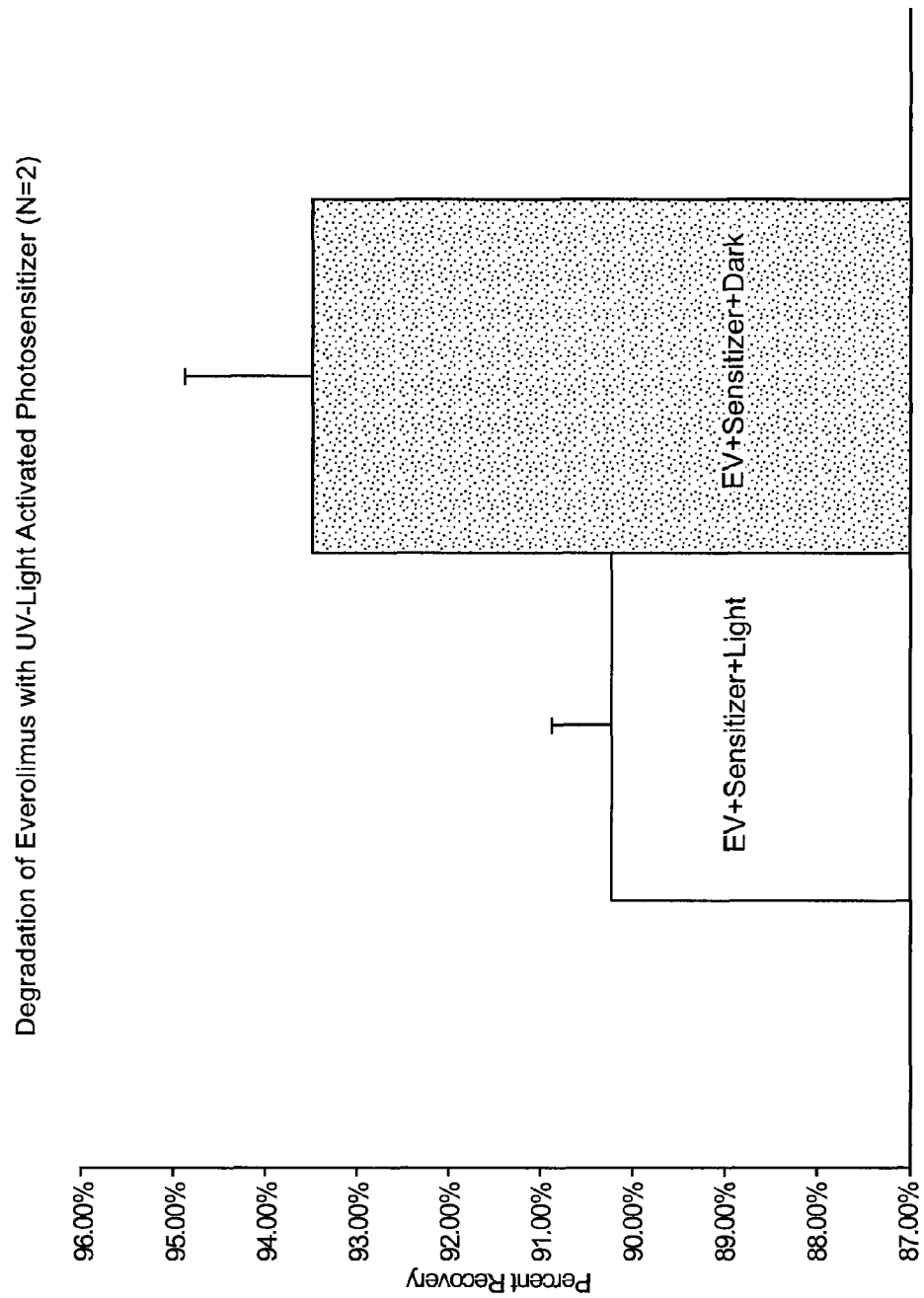
FIG. 8 is a bar-chart showing the effectiveness of drug degradation using light for Everolimus combined with a photosensitizer in a solution of methanol.

FIG. 8 is a bar-chart showing the effectiveness of drug degradation using light. The tests were conducted on Everolimus combined with a photosensitizer in a solution of methanol. After a sufficient number of trials were conducted, a mean and standard deviation of the percent recovery for Everolimus was computed for each of two cases (as shown). The first case corresponds to the percent recovery of Everolimus without exposing the solution to UV light energy (referred to as "EV+Sensitizer+Dark") and the second case corresponds to the percent recovery of Everolimus when the solution is exposed to UV light energy (referred to as "EV+Sensitizer+Light"). As can be seen, there is more than a 3% reduction in the potency of Everolimus after the solution was exposed to UV light.

In some embodiments it may be important or at least desirable to achieve a 100% degradation, so that one has absolute control over what tissue is exposed to the drug and which is not. However, depending on the rate of drug degradation, the toxicity of the degradation products, light penetration into the tissue, etc., it may be difficult or even undesirable to achieve 100%. In other embodiments, one may attempt to reduce the amount of drug to a level out of its beneficial therapeutic range, or specifically to a level below that which produces the undesirable effects we would like to prevent with this technique. The percent degradation would depend on the original drug dosing (amount of drug in the tissue) and the therapeutic window of the drug.

In one example, a sample available drug was used, which can be Everolimus. The drug was mixed with a photosensitizer in methanol, and exposed to a low intensity laser light source at the wavelength used to activate the photosensitizer. The dark and light samples were then sent for analysis of total drug concentration via HPLC (total content assay), which gives how much drug is contained in a specific volume of solution. The percent recovery is measured as the concentration of drug recovered divided by the original concentration of the solution. A low (3%) difference, as depicted in the illustrative example, may be due to a multitude of factors. For example, the amount of drug used in the experiment may be so great as to not reflect a noticeable difference between the exposed and unexposed. A concentration of 1.5 mg/ml of Everolimus was used in 18 ml of methanol, which means a total drug content of 27 mg . . . a typical 28 mm stent contains about 130 ug of Everolimus, which would be much more sensitive for a small change in drug content. The laser light source used was of a much lower power (25 mW) than one that would be used in clinical practice (500 mW), but which was compensated for by applying a longer exposure time to equal the comparable light dose that would be used in the clinic. The long experiment time may lead to a greater amount of natural degradation in the control (dark) sample, and when considering that the laser is of a low power to cause any additional degradation, a difference between the two in the illustrated example may not be as significant.

An ideal drug for use would contain a linkage which would make it more sensitive to either to degradation via light exposure or a degradation reaction with a reactive oxygen species triggered by light exposure to the photosensitizer.

Figure 6:
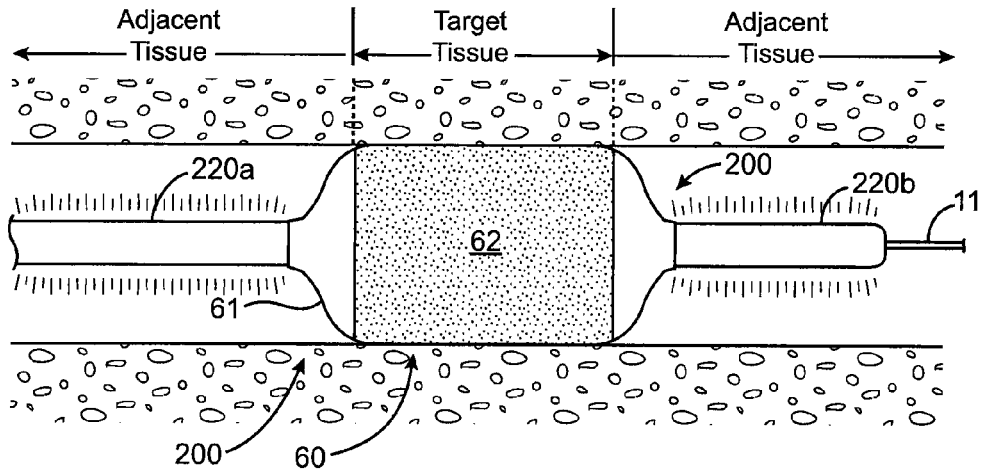
FIG. 6 is a side view of a distal portion of a second embodiment of a balloon catheter located at a treatment area according to the disclosure.

A catheter adapted for being used in a manner consistent with the disclosure may also be configured with light-emitting members located proximal, distal or proximal and distal of a balloon assembly. For example, a catheter 200 depicted in FIG. 6 includes light emitting members 220a and 220b located proximal and distal of balloon assembly 60. Light emitting members 220a, 220b may be used to degrade drug that is diffused into, or otherwise comes in contact with the adjacent tissue. The target tissue is treated with the drug at full potency when the balloon places surface 62 (containing the drug—sensitizer combination) against the target tissue. When the light emitting members (e.g., respective distal and proximal portion(s) 220a, 220b of catheter shaft, which may include diffusion lenses coupled to fiber optics or one or more LED array(s)) are activated, the light, e.g., UV light, degrades the potency of the drug that is present in the adjacent tissue. One benefit of a catheter constructed in accordance with the embodiments relating to FIG. 6 is that a greater amount of adjacent tissue may be treated with light.

Figure 7:
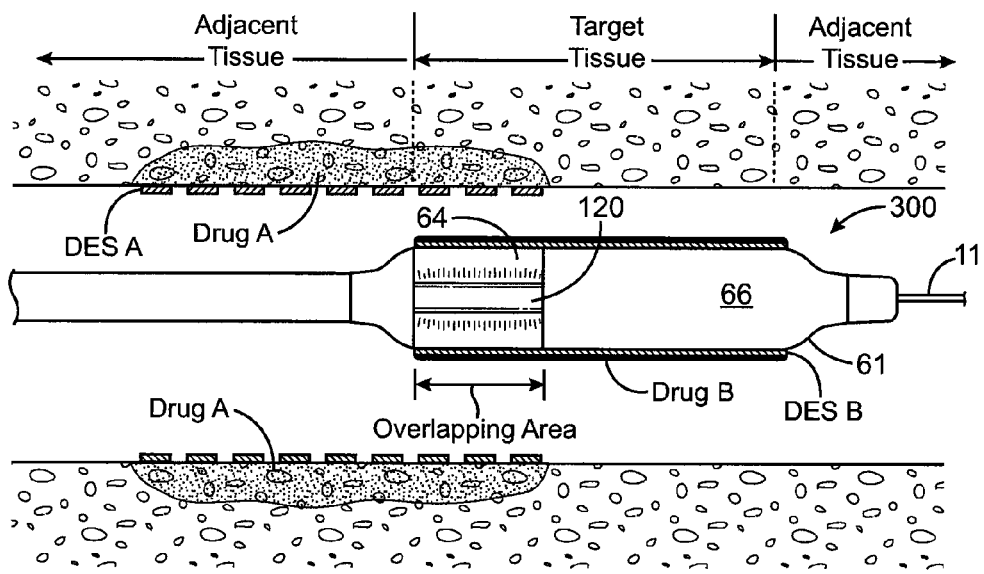
FIG. 7 is a side view of is a side view of a distal portion of a third embodiment of a stent delivery catheter and prior implanted stent located at a treatment area according to the disclosure.

In other embodiments, a balloon catheter according to the disclosure may be used in connection with the delivery of Drug Eluting Stents (DES). For example, a catheter may be configured to prevent or mitigate the mixing of drugs carried by two DES, or reduce instances of double-dosing of the same drug when a DES is placed adjacent to another, previously implanted DES, or when portions of these stents overlap each other. Referring to the example depicted in FIG. 7, a catheter 300 delivers DES B to a treatment area. DES B carries a DRUG B on its outer surface and will be implanted adjacent a previously implanted DES A. This stent carried a DRUG A which has begun to perfuse into the tissue (as shown).

A balloon assembly 60 portion of catheter 300, which carries DES B to the treatment site, may include a light-blocking portion 66 of the balloon membrane 61 and a filter, light admitting or window 64 located at the proximal end, distal end or both ends of the balloon (also corresponding to ends of DES B). The length of the window(s) 64 may correspond to the amount of overlap intended between the two stents, or the expected amount (or rate) of diffusion of DRUG A and/or DRUG B after the second stent has been implanted. DES B may span over the window or light emitting portion of the balloon, or the catheter may have a second light emitting portion adjacent one or both ends of DES B for illuminating areas adjacent DES A. In some embodiments DES A may be provided from the same stent provider as DRUG B, or a different provider. DRUG A may be the same as DRUG B or different. In some embodiments a stent delivery catheter may include windows at both ends to reduce the appearance of "end effects" as discussed earlier.

Referring again to the balloon catheter of FIG. 5, in some embodiments the portion 62 may permit a first wavelength of light to pass through the membrane walls to reach the target tissue, while portions 64 permit a second wavelength to pass through the membrane walls to reach adjacent, healthy tissue. For example, a first portion of a balloon membrane may permit only NIR light to pass through the walls whereas a second portion allows all light to reach tissue. Referring again to FIG. 6, in a variation of the catheter 200, one or more light sources produce light at light member(s) 220 and within the balloon chamber 7a (see FIG. 1). The light emitted from light member(s) 220 and from within the balloon chamber 7a may be broad band light. The balloon membrane, however, permits only a narrow band of light from passing through its walls, e.g., NIR. In these examples a drug-coated balloon catheter (or DES) may use light to both activate a photosensitive drug in target tissue and degrade that drug's potency in adjacent healthy tissue. These embodiments may be especially useful when treating tumors.

In accordance with the foregoing embodiments, a treatment agent can include, but is not limited to, an anti-proliferative, an anti-inflammatory or immune modulating agent, an anti-migratory, an anti-thrombotic or other pro-healing agent or a combination thereof.

The anti-proliferative agent can be a natural proteineous agent such as cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin C1); all taxoids such as taxols, docetaxel, and paclitaxel, and paclitaxel derivatives; all olimus drugs including macrolide antibiotics such as tacrolimus, rapamycin (i.e., sirolimus) derivatives of which include 40-O-[2-(2-hydroxy)ethoxy]ethyl-rapamycin, 40-O-(3-hydroxy)propyl-rapamycin, 40-O-tetrazole-rapamycin, 40-epi-(N1-tetrazolyl)-rapamycin (ABT-578 manufactured by Abbott Laboratories, Abbott Park, Ill.); everolimus (i.e., RAD-001); FKBP-12 mediated mTOR inhibitors, perfenidone and prodrugs, co-drugs and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone diproprionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen fenclofenac, fenclorac, fendosal, fenpipalone, fentiazac, flazalone, fluazocort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone sodium glycerate, perfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicyclic acid), salicyclic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant and/or cytostatic (i.e. cell-suppressing) properties. Examples of suitable treatment and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol Myers Squibb Co, Stamford, Conn.). Examples of such antiplatelets, anticoagulants, antifebrin, antithrombins include sodium heparin, low molecular weight heparins, heparinoids, hirudin, argatroban, forskolin, vapiprost, prostacyclin, and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc. Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, dietary supplements such as various vitamins, and a combination thereof. Examples of cytostatic substances include angiopeptin, angiotensin converting enzyme inhibitors such as captopril (e.g., Capoten® and Capozide® from Bristol Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include α-interferon, and genetically engineered epithelial cells. The foregoing substances are listed by way of example and are not meant to be limiting. Other treatment agents which are currently available or that may be developed in the future are equally applicable.

In accordance with the foregoing embodiments, the reactive oxygen producing and light emitting photosensitizers include, but are no limited to: Pyrrole-derived macrocyclic compounds, naturally occurring or synthetic porphyrins or derivatives thereof, naturally occurring or synthetic chlorines and derivatives thereof, naturally occurring or synthetic bacteriochlorins and derivatives thereof, synthetic isobacteriochlorins and derivatives thereof, phthalocyanines and derivatives thereof, naphthalocyaniines and derivatives thereof, porphycenes and derivatives thereof, naphthalocyanines and derivatives thereof, porphycyanines and derivatives thereof, pentaphyrin and derivatives thereof, sapphyrins and derivatives thereof, texaphyrins and derivatives thereof, phenoxazine dyes and derivatives thereof, phenothiazines and derivatives thereof, chalcoorganapyrylium dyes and derivatives thereof, triarylmethanes and derivatives thereof, rhodamines and derivatives thereof, fluorescenes and derivatives thereof, azaporphyrins and derivatives thereof, benzochlorins and derivatives thereof, purpurins and derivatives thereof, chlorophylls and derivatives thereof, squaraines and derivatives thereof, hypericin and derivatives thereof, verdins and derivatives thereof, xanthenes and derivative thereof, etc.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A catheter having distal and proximal portions, comprising:
   a balloon, or a balloon and stent, located at the distal portion, the balloon or stent, respectively, configured for being placed in contact with tissue; and
   a light emitting member located adjacent the balloon, including a plurality of light-emitters and light detectors;
   computer implemented logic for performing steps (a) and (b) for each of the plurality of light-emitters:
      (a) activate the light emitter, and
      (b) detect an intensity of reflected light received at the plurality of light detectors, wherein a light detector is paired with the activated light emitter when the light detector has a highest intensity of reflected light for the plurality of light detectors; and
   a control system configured for initiating photodynamic therapy (PDT) based on a detected presence of abnormal tissue such that the control system is configured to activate or deactivate a plurality of light-emitters based on a detected variation in reflected light intensity among the respective plurality of light detectors paired with the light-emitters, wherein the variation in reflected light intensity indicates the locations where abnormal tissue opposes light emitters.

2. A catheter having distal and proximal portions and configured for treating tissue in a treatment area with light therapy, comprising:
   a plurality of light-emitters and light detectors;
   means for pairing the light emitters with the light detectors based on the intensity of reflective light received at the light detectors when the light emitters are activated;
   light detectors paired with each of the light emitters such that a light detector detects light reflected from tissue receiving light emitted substantially from the paired light emitter; and
   a controller for exposing only abnormal tissue in the treatment area to the light therapy;
   wherein the controller is configured to activate the plurality of light emitters, receive a signal from each of the light detectors in response to light reflected from tissue, and deactivate any light emitter paired with a light detector that has a signal greater than a predetermined value.

3. The catheter of claim 1, wherein the controller is further configured to execute a calibration routine for distinguishing between healthy and abnormal tissue opposing the pairs of light emitters and light detectors when the balloon, or balloon and stent, are placed in contact with tissue, including the steps of activating the light emitters, receiving a signal from each of the light detectors in response to the light emitted from the adjacent light emitters, followed by deactivation of any light emitter having a corresponding light detector signal that is greater than a predetermined value.

4. A catheter having distal and proximal portions and configured for treating tissue in a treatment area with light therapy, comprising:
   an array of light-emitting diode (LED)—photodiode pairs, wherein the LED is activated or deactivated based on light detected at the paired photodiode; and
   a controller for initiating the light therapy using only those LEDs not deactivated based on light received at the respective paired photodiode.

5. The catheter of claim 4, wherein the array of LED—photodiode pairs comprise computer-implemented logic for activating or deactivating an LED based on a magnitude of a signal received from its paired photodiode.

6. The catheter of claim 5, wherein the array of LED—photodiode pairs further comprise a circuit disposed at the distal portion of the catheter and configured for implementing the logic for activating or deactivating the LED.

7. The catheter of claim 4, wherein the controller is configured for pairing a photodiode with an LED, thereby producing the LED-photodiode pair, based on a comparison of signals received from each of a plurality of photodiodes when the LED is activated.

8. The catheter of claim 1, wherein the light emitters are light-emitting diodes (LEDs).

9. The catheter of claim 2, wherein the light emitters are light-emitting diodes (LEDs).

* * * * *